United States Patent
Pierce

(10) Patent No.: US 6,251,176 B1
(45) Date of Patent: Jun. 26, 2001

(54) ALGINATE FLAVORING IN A POWDERED FORM

(76) Inventor: Karen A. Pierce, 14747 Artesia Blvd. Bldg 5, Unit N, La Mirada, CA (US) 90638

( * ) Notice: Subject to any disclaimer, the term of this patent is extended or adjusted under 35 U.S.C. 154(b) by 0 days.

(21) Appl. No.: 09/441,276

(22) Filed: Nov. 16, 1999

(51) Int. Cl.⁷ .................................. C08L 5/04; A61K 6/10
(52) U.S. Cl. ............................. 106/35; 523/109; 524/28; 536/3
(58) Field of Search .................. 536/3; 524/28; 523/109; 106/35

(56) References Cited

U.S. PATENT DOCUMENTS

| | | | |
|---|---|---|---|
| 4,381,947 | 5/1983 | Pellico | 106/35 |
| 4,515,913 | 5/1985 | Pellico | 523/109 |
| 4,543,372 | 9/1985 | Watanabe et al. | 523/109 |
| 4,590,077 | 5/1986 | Trop | 426/61 |
| 4,603,054 | 7/1986 | Schmidt et al. | 426/574 |
| 4,626,558 | 12/1986 | Pellico | 523/109 |
| 4,670,053 | 6/1987 | Kooke et al. | 106/35 |
| 4,689,079 | 8/1987 | Buma et al. | 106/35 |
| 4,695,322 | 9/1987 | Schwabe et al. | 106/35 |
| 4,869,902 * | 9/1989 | Buehler et al. | 424/686 |
| 4,979,989 | 12/1990 | Ridoux | 106/35 |
| 5,076,790 | 12/1991 | Rollison et al. | 433/214 |
| 5,153,317 | 10/1992 | Ortega et al. | 8/543 |
| 5,252,351 | 10/1993 | Cox et al. | 426/549 |
| 5,902,622 | 5/1999 | Owusu-Ansah et al. | 426/429 |

OTHER PUBLICATIONS

Replica promotional flyer, copyright Matech, Inc., 1989.
Express Dental Products Catalog 001–001, p. 8.
Express Dental Products promotional flyer, "Lab Pack".

* cited by examiner

*Primary Examiner*—Peter Szekely
(74) *Attorney, Agent, or Firm*—Charles H. Thomas

(57) ABSTRACT

An otherwise conventional powdered alginate impression material is improved by the admixture of flavoring in powdered form, rather than liquid form. By utilizing a powdered flavoring, rather than a liquid flavoring, the components of the dental impression material can remain totally in powdered form until mixed with water in an orthodontic office immediately prior to taking a dental impression. By providing the flavoring for the powdered alginate material in powdered form, the shipment of any component of the alginate impression material in liquid form is avoided. As a consequence, the powdered flavoring material for the alginate impression composition is not susceptible to liquid leakage and does not create a disagreeable, sticky mess even if the container is broken during shipment.

7 Claims, No Drawings

ALGINATE FLAVORING IN A POWDERED FORM

BACKGROUND OF THE INVENTION

1. Field of the Invention

The present invention relates to flavored orthodontic impression substances containing alginate.

2. Description of the Prior Art

In order to create dental crowns and orthodontic dentures it is necessary for an orthodontist to take an impression of the patient's existing teeth to which the crowns or dentures are to be mounted. A dental impression is created from a curable material which is placed in a mold. The mold is then placed in the patient's mouth whereupon the patient bites down into the mold. The impression material must be sufficiently amorphous in its initial state so as to yield in a completely inelastic manner and conform completely to the size and shape of the patient's existing teeth. However, the dental impression material must readily cure within a very short period of time so as to preserve the impression created once the patient releases his or her bite into the impression material. Moreover, the impression material cannot be in any way toxic since it is designed to be placed within a patient's mouth.

Dental impression substances employing alginate as the primary curing material are widely utilized in the orthodontic profession for creating dental impressions. Alginate is a substance made out of ground seaweed. In the orthodontic industry it is pulverized, sanitized, and made into a gel. Agar agar is used as a thickener in the production of the alginate substance utilized for making dental impressions.

At present, alginate is mixed with a liquid form of food flavoring when it is used for the purpose of creating dental impressions, since the taste of unflavored alginate causes a significant number of dental patients to gag. By mixing the alginate with liquid food flavoring, the unpleasant taste of the alginate is masked, thus resulting in fewer problems of faulty dental impressions due to patient gagging.

One big problem with the conventional liquid form of food flavoring utilized in an alginate material used to form dental impressions is that the liquid form of food flavoring cannot be shipped internationally. The reason is because the packaging containing the liquid food flavoring can break, thus creating a mess that is very difficult to deal with. Customs regulations of some countries prohibit or severely restrict the shipment of food flavoring in liquid form.

SUMMARY OF THE INVENTION

According to the present invention a system has been devised that employs a powdered alginate flavoring which is mixed with alginate that is also in powdered form. Because the flavoring substance remains in a powdered form during shipment, it is not susceptible to leakage nor does it create messes like conventional liquid food flavorings for dental alginate impression substances. Therefore, it can be shipped internationally. Once the powdered substance arrives at the dental office, it is mixed with water along with a powdered alginate impression material so that the flavored orthodontic impression material can be utilized in a conventional manner.

In one broad aspect the present invention may be considered to be an improvement in a powdered orthodontic impression composition including alginate and comprising a flavoring in powdered form. Preferably the powdered orthodontic impression composition is comprised of between four percent and about seven percent by weight of the powdered flavoring.

In another broad aspect the invention may be considered to be an improvement in a powdered orthodontic impression composition including alginate and a flavoring substance. Such a composition is improved in that the flavoring substance is present in powdered form. Preferably the powdered composition is comprised of between four percent and about seven percent of the powdered flavoring by weight prior to the addition of water.

In another broad aspect the invention may be considered to be an improvement in a method of creating a dental impression in which a powered orthodontic impression substance containing alginate is mixed with a liquid to form a curable gel. According to the improvement of the invention a powdered flavoring is added to the powdered orthodontic impression substance prior to or during the addition of the liquid, which is normally water. Preferably the powdered flavoring is added to the extent of between about one percent and ten percent by weight prior to the addition of water. Once the powdered flavoring has been added to the powdered orthodontic impression substance, the powdered mixture is mixed with water. Preferably three measures of the powdered dental impression material plus one teaspoon of powdered flavoring are mixed with one measure of water to form a suitable amount of curable flavored dental impression material to create an impression of the existing teeth and dentures of the upper jaw of a patient. Two measures of the powdered composition are mixed with one measure of water to create a suitable amount of curable dental impression material for the existing teeth and dentures of the lower jaw of a patient. Each measure is two table spoons in volume.

The invention may be described with greater clarity and particularity by reference to the following illustrative examples.

EXAMPLE I

Three measures of an alginate impression material are placed in a generally U-shaped mold of the type conventionally used to take dental impressions of orthodontic patients. The powdered dental impression composition may, for example, be a powdered alginate mixture sold as Replica alginate impression material by Matech, Inc., located at 13101 San Fernando Road, Sylmar, Calif. 91342. This dental impression material is comprised of the following ingredients:

| | |
|---|---|
| Alginate | 16% |
| Magnesium Oxide | 12% |
| Calcium Oxide | 11% |
| Potassium Titanium Fluoride | 4% |
| Sodium Phosphate | 2% |
| Diatomaceous Earth | 57% |

This substance is sold in bulk in a fme powder form. Each measure of this alginate impression material weighs about seven grams.

One teaspoon of powdered flavoring is added to the three measures of the Replica alginate impression material. The powdered flavoring may, for example, be bubble gum flavored powder sold by Flavor Producers Inc., located at 12350 Montague Street, Arleta, Calif. 91331.

The powdered flavoring is mixed throughly into the measures of Replicate alginate impression material in the tray by stirring with a teaspoon or other implement. Once the powdered flavoring has been throughly mixed into the powdered alginate impression material, one measure of water is added to the powder mixture and the material is then stirred some more for a few seconds until it has a uniform gel consistency.

The U-shaped dental impression tray is then placed in the patient's mouth with the open side facing upwardly. The patient is instructed to bite down firmly into the mixture until the gel solidifies, which takes approximately two to three minutes. The patient is instructed not to move his or her jaws during that time.

Without any flavoring, the alginate material has a taste and aroma that will frequently cause the patient to gag or move his or her jaws relative to the tray. The flavoring in the alginate material quells any such reaction, however. After about three minutes at the most, the patient is instructed to separate his or her jaws slowly, and the tray is removed, leaving a very accurate impression of the existing teeth in the jaw.

EXAMPLE II

Two measures of the same Replica alginate impression material are placed in a dental impression tray. Each measure of the powdered alginate material weighs about seven grams. To this amount of alginate impression material one teaspoon of powdered watermelon flavoring obtained from Flavor Producers Inc. is added. The powdered flavoring material is mixed into the powdered alginate material using a spoon or some other stirring implement. One measure of water is then added and the mixture is again stirred for a few seconds until the gel has formed a uniform consistency.

The tray is then inverted and placed in the patient's mouth atop the upper teeth and dentures of the patient. The patient is again instructed to firmly bite down on the tray to create an impression of the lower set of teeth in the alginate material and then not to move his or her jaws. After two to three minutes the gel-like alginate impression material with flavoring added has cured. The patient then releases his or her bite and the tray is removed. The impression left is an accurate reproduction of the space occupied by the patient's existing lower teeth and dentures.

EXAMPLE III

The steps of Example II are repeated but with the substitution of powdered strawberry flavoring for the watermelon flavoring.

It is to be understood that numerous variations and modifications of the invention will become readily apparent to those familiar with alginate dental impression materials. For example, other types of dental impression substances containing alginate may be substituted for the Replica alginate impression material. Also, the relative quantities of powdered flavoring that are mixed with the powdered alginate relative quantities of powdered flavoring that are mixed with the powdered alginate impression material may be varied over a wide range. It is necessary only for a sufficient amount of powdered flavoring material to be present so as to produce a flavor and aroma strong enough to overcome any tendency for the patient to gag or otherwise react negatively to the powdered alginate impression material. Also, virtually any different type of powdered flavoring material which is acceptable for use in foods may be utilized for purposes of the invention. Accordingly, the scope of the invention should not be construed as limited to the specific examples described.

What is claimed is:

1. In a method of creating a dental impression in which a powdered orthodontic impression substance containing alginate is mixed with a liquid to form a curable gel, the improvement comprising: adding to said powdered orthodontic impression substance a powdered flavoring.

2. A method according to claim 1 wherein said powdered flavoring is added to said powdered orthodontic impression substance to the extent of between about one percent and ten percent by weight.

3. A method according to claim 1 wherein said powdered flavoring is added to said powdered orthodontic impression substance to the extent of between about four percent and seven percent by weight.

4. A powdered orthodontic impression composition including alginate and comprising a flavoring in powdered form.

5. A orthodontic impression composition according to claim 4 comprising between about four percent and about seven percent by weight of said flavoring.

6. In a powdered orthodontic impression composition including alginate and a flavoring substance the improvement wherein said flavoring substance is present in powdered form.

7. A powdered orthodontic impression composition according to claim 6 comprising between about four percent and about seven percent of said flavoring by weight.

* * * * *